(12) United States Patent
Govari

(10) Patent No.: US 8,920,415 B2
(45) Date of Patent: Dec. 30, 2014

(54) CATHETER WITH HELICAL ELECTRODE

(75) Inventor: Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 820 days.

(21) Appl. No.: 12/639,096

(22) Filed: Dec. 16, 2009

(65) Prior Publication Data

US 2011/0144639 A1    Jun. 16, 2011

(51) Int. Cl.
  *A61B 18/14*    (2006.01)
  *A61B 17/32*    (2006.01)
  *A61B 18/18*    (2006.01)
  *A61B 18/00*    (2006.01)

(52) U.S. Cl.
  CPC ..... *A61B 18/1492* (2013.01); *A61B 17/320068* (2013.01); *A61B 18/1815* (2013.01); *A61B 2018/00011* (2013.01); *A61B 2018/1407* (2013.01); *A61B 2018/1435* (2013.01); *A61B 2018/1861* (2013.01); *A61B 2218/002* (2013.01)
  USPC .............................................. 606/41; 606/49

(58) Field of Classification Search
  USPC .............................. 606/32, 41, 49
  See application file for complete search history.

(56) References Cited

U.S. PATENT DOCUMENTS

| 3,971,364 A | 7/1976 | Fletcher et al. |
| 4,488,561 A | 12/1984 | Doring |
| 4,764,114 A | 8/1988 | Jeffcoat et al. |
| 4,856,993 A | 8/1989 | Maness et al. |
| 4,917,102 A | 4/1990 | Miller et al. |
| 4,917,104 A | 4/1990 | Rebell |
| 5,263,493 A | 11/1993 | Avitall |
| 5,334,193 A * | 8/1994 | Nardella .................... 606/41 |
| 5,368,564 A | 11/1994 | Savage |
| 5,391,199 A | 2/1995 | Ben Haim |
| 5,487,757 A | 1/1996 | Truckai et al. |
| 5,499,542 A | 3/1996 | Morlan |
| 5,558,091 A | 9/1996 | Acker et al. |
| 5,563,354 A | 10/1996 | Kropp |
| 5,643,197 A | 7/1997 | Brucker |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,730,127 A | 3/1998 | Avitall |
| 5,769,843 A | 6/1998 | Abela et al. |
| 5,820,591 A | 10/1998 | Thompson et al. |
| 5,826,576 A | 10/1998 | West |
| 5,836,894 A | 11/1998 | Sarvazyan |

(Continued)

FOREIGN PATENT DOCUMENTS

| DE | 19750441 A | 6/1999 |
| EP | 0856292 A1 | 8/1998 |

(Continued)

OTHER PUBLICATIONS

EP 12157864.5—2305 Search Report dated Apr. 16, 2012.

(Continued)

*Primary Examiner* — Linda Dvorak
*Assistant Examiner* — Jocelyn D Ram

(57) ABSTRACT

An invasive probe includes an insertion tube containing a lumen for providing an irrigation fluid and comprising a distal portion having a plurality of perforations therethrough providing fluid communication between the lumen and an outer surface of the insertion tube. At least one helical electrode is fitted over the distal portion of the insertion tube.

15 Claims, 4 Drawing Sheets

(56) References Cited

U.S. PATENT DOCUMENTS

| | | | | |
|---|---|---|---|---|
| 5,860,920 | A | 1/1999 | McGee et al. | |
| 5,860,974 | A | 1/1999 | Abele | |
| 5,865,815 | A | 2/1999 | Tihon | |
| 5,871,523 | A | 2/1999 | Fleischman et al. | |
| 5,876,398 | A * | 3/1999 | Mulier et al. | 606/41 |
| 5,902,248 | A | 5/1999 | Millar et al. | |
| 5,916,147 | A | 6/1999 | Boury | |
| 5,938,694 | A | 8/1999 | Jaraczewski et al. | |
| 5,944,022 | A | 8/1999 | Nardella et al. | |
| 5,964,757 | A | 10/1999 | Ponzi | |
| 5,974,320 | A | 10/1999 | Ward et al. | |
| 5,983,126 | A | 11/1999 | Wittkampf | |
| 6,002,955 | A | 12/1999 | Willems et al. | |
| 6,048,329 | A | 4/2000 | Thompson et al. | |
| 6,063,022 | A | 5/2000 | Ben Haim | |
| 6,064,902 | A | 5/2000 | Haissaguerre et al. | |
| 6,123,699 | A | 9/2000 | Webster, Jr. | |
| 6,171,277 | B1 | 1/2001 | Ponzi | |
| 6,177,792 | B1 | 1/2001 | Govari et al. | |
| 6,183,463 | B1 | 2/2001 | Webster, Jr. | |
| 6,198,974 | B1 | 3/2001 | Webster, Jr. | |
| 6,201,387 | B1 | 3/2001 | Govari | |
| 6,203,493 | B1 | 3/2001 | Ben Haim | |
| 6,216,027 | B1 | 4/2001 | Willis et al. | |
| 6,226,542 | B1 | 5/2001 | Reisfeld | |
| 6,239,724 | B1 | 5/2001 | Doron et al. | |
| 6,241,724 | B1 | 6/2001 | Fleischman et al. | |
| 6,267,781 | B1 | 7/2001 | Tu | |
| 6,272,371 | B1 | 8/2001 | Shlomo | |
| 6,272,672 | B1 | 8/2001 | Conway | |
| 6,301,496 | B1 | 10/2001 | Reisfeld | |
| 6,332,089 | B1 | 12/2001 | Acker et al. | |
| 6,335,617 | B1 | 1/2002 | Osadchy et al. | |
| 6,371,955 | B1 | 4/2002 | Fuimaono et al. | |
| 6,436,059 | B1 | 8/2002 | Zanelli | |
| 6,456,864 | B1 | 9/2002 | Swanson et al. | |
| 6,468,260 | B1 | 10/2002 | Bumbalough et al. | |
| 6,484,118 | B1 | 11/2002 | Govari | |
| 6,500,167 | B1 | 12/2002 | Webster, Jr. | |
| 6,522,933 | B2 | 2/2003 | Nguyen | |
| 6,551,302 | B1 | 4/2003 | Rosinko et al. | |
| 6,574,492 | B1 | 6/2003 | Ben Haim et al. | |
| 6,584,856 | B1 | 7/2003 | Biter et al. | |
| 6,592,581 | B2 | 7/2003 | Bowe | |
| 6,602,242 | B1 | 8/2003 | Fung et al. | |
| 6,612,992 | B1 | 9/2003 | Hossack et al. | |
| 6,618,612 | B1 | 9/2003 | Acker et al. | |
| 6,669,692 | B1 * | 12/2003 | Nelson et al. | 606/41 |
| 6,690,963 | B2 | 2/2004 | Ben Haim et al. | |
| 6,695,808 | B2 | 2/2004 | Tom | |
| 6,711,429 | B1 | 3/2004 | Gilboa et al. | |
| 6,712,815 | B2 * | 3/2004 | Sampson et al. | 606/41 |
| 6,723,094 | B1 | 4/2004 | Desinger | |
| 6,727,371 | B2 | 4/2004 | Müller et al. | |
| 6,814,733 | B2 | 11/2004 | Schwartz et al. | |
| 6,835,173 | B2 | 12/2004 | Couvillon, Jr. | |
| 6,892,091 | B1 | 5/2005 | Ben Haim et al. | |
| 6,908,464 | B2 | 6/2005 | Jenkins et al. | |
| 6,911,019 | B2 | 6/2005 | Mulier et al. | |
| 6,915,149 | B2 | 7/2005 | Ben Haim | |
| 6,945,956 | B2 | 9/2005 | Waldhauser et al. | |
| 6,964,205 | B2 | 11/2005 | Papakostas et al. | |
| 6,973,339 | B2 | 12/2005 | Govari | |
| 6,997,924 | B2 | 2/2006 | Schwartz et al. | |
| 7,008,401 | B2 | 3/2006 | Thompson et al. | |
| 7,008,418 | B2 | 3/2006 | Hall et al. | |
| 7,077,823 | B2 | 7/2006 | McDaniel | |
| 7,156,816 | B2 | 1/2007 | Schwartz et al. | |
| 7,235,070 | B2 | 6/2007 | Vanney | |
| 7,285,119 | B2 | 10/2007 | Stewart et al. | |
| 7,306,593 | B2 | 12/2007 | Keidar et al. | |
| 7,311,704 | B2 | 12/2007 | Paul et al. | |
| 7,397,364 | B2 | 7/2008 | Govari | |
| 7,419,489 | B2 * | 9/2008 | Vanney et al. | 606/41 |
| 7,481,774 | B2 | 1/2009 | Brockway et al. | |
| 7,517,349 | B2 | 4/2009 | Truckai et al. | |
| 7,536,218 | B2 | 5/2009 | Govari et al. | |
| 7,604,605 | B2 | 10/2009 | Zvuloni | |
| 7,681,432 | B2 | 3/2010 | Hay et al. | |
| 7,686,767 | B2 | 3/2010 | Maschke | |
| 8,066,702 | B2 * | 11/2011 | Rittman et al. | 606/41 |
| 8,083,691 | B2 | 12/2011 | Goldenberg et al. | |
| 8,628,526 | B2 * | 1/2014 | Laufer et al. | 606/41 |
| 2001/0007070 | A1 * | 7/2001 | Stewart et al. | 606/41 |
| 2001/0047129 | A1 | 11/2001 | Hall et al. | |
| 2001/0047133 | A1 | 11/2001 | Gilboa et al. | |
| 2002/0002329 | A1 | 1/2002 | Avitall | |
| 2002/0022839 | A1 | 2/2002 | Stewart et al. | |
| 2002/0065455 | A1 | 5/2002 | Ben Haim et al. | |
| 2002/0068866 | A1 | 6/2002 | Zikorus et al. | |
| 2002/0165461 | A1 | 11/2002 | Hayzelden et al. | |
| 2002/0193781 | A1 | 12/2002 | Loeb | |
| 2003/0105453 | A1 | 6/2003 | Stewart et al. | |
| 2003/0120195 | A1 | 6/2003 | Milo et al. | |
| 2003/0130615 | A1 | 7/2003 | Tom | |
| 2003/0158494 | A1 | 8/2003 | Dahl et al. | |
| 2003/0216722 | A1 * | 11/2003 | Swanson | 606/32 |
| 2004/0049255 | A1 | 3/2004 | Jain et al. | |
| 2004/0064024 | A1 | 4/2004 | Sommer | |
| 2004/0068178 | A1 | 4/2004 | Govari | |
| 2004/0082948 | A1 | 4/2004 | Stewart et al. | |
| 2004/0097806 | A1 | 5/2004 | Hunter et al. | |
| 2004/0102769 | A1 | 5/2004 | Schwartz et al. | |
| 2004/0143175 | A1 | 7/2004 | Coleman et al. | |
| 2004/0147920 | A1 | 7/2004 | Keidar | |
| 2004/0152974 | A1 | 8/2004 | Solomon et al. | |
| 2004/0244464 | A1 | 12/2004 | Hajdukiewicz et al. | |
| 2004/0254458 | A1 | 12/2004 | Govari | |
| 2005/0004565 | A1 | 1/2005 | Vanney | |
| 2005/0010095 | A1 | 1/2005 | Stewart et al. | |
| 2005/0033135 | A1 | 2/2005 | Govari | |
| 2005/0070894 | A1 | 3/2005 | McClurken | |
| 2005/0080429 | A1 | 4/2005 | Freyman et al. | |
| 2005/0187544 | A1 | 8/2005 | Swanson | |
| 2005/0277875 | A1 | 12/2005 | Selkee | |
| 2006/0009690 | A1 | 1/2006 | Fuimaono et al. | |
| 2006/0009735 | A1 | 1/2006 | Viswanathan et al. | |
| 2006/0015096 | A1 | 1/2006 | Hauck et al. | |
| 2006/0020264 | A1 * | 1/2006 | Crowley et al. | 606/41 |
| 2006/0106295 | A1 | 5/2006 | Jais et al. | |
| 2006/0173480 | A1 | 8/2006 | Zhang | |
| 2006/0200049 | A1 | 9/2006 | Leo et al. | |
| 2006/0235381 | A1 * | 10/2006 | Whayne et al. | 606/49 |
| 2006/0247618 | A1 | 11/2006 | Kaplan et al. | |
| 2006/0253116 | A1 | 11/2006 | Avitall et al. | |
| 2007/0021742 | A1 | 1/2007 | Viswanathan | |
| 2007/0060832 | A1 | 3/2007 | Levin | |
| 2007/0060847 | A1 | 3/2007 | Leo et al. | |
| 2007/0100332 | A1 | 5/2007 | Paul et al. | |
| 2007/0106114 | A1 | 5/2007 | Sugimoto et al. | |
| 2007/0142749 | A1 | 6/2007 | Khatib et al. | |
| 2007/0151391 | A1 | 7/2007 | Larkin et al. | |
| 2007/0156114 | A1 | 7/2007 | Worley et al. | |
| 2007/0161882 | A1 | 7/2007 | Pappone | |
| 2007/0179492 | A1 | 8/2007 | Pappone | |
| 2007/0185397 | A1 | 8/2007 | Govari et al. | |
| 2007/0191829 | A1 | 8/2007 | McGee et al. | |
| 2007/0197939 | A1 | 8/2007 | Wallace et al. | |
| 2007/0282211 | A1 | 12/2007 | Ofek et al. | |
| 2008/0009750 | A1 | 1/2008 | Aeby et al. | |
| 2008/0015568 | A1 | 1/2008 | Paul et al. | |
| 2008/0051704 | A1 | 2/2008 | Patel et al. | |
| 2008/0065111 | A1 | 3/2008 | Blumenkranz et al. | |
| 2008/0071267 | A1 | 3/2008 | Wang et al. | |
| 2008/0077049 | A1 | 3/2008 | Hirshman | |
| 2008/0097394 | A1 | 4/2008 | Lampropoulos et al. | |
| 2008/0161774 | A1 | 7/2008 | Hastings et al. | |
| 2008/0161795 | A1 | 7/2008 | Wang et al. | |
| 2008/0183075 | A1 | 7/2008 | Govari et al. | |
| 2008/0249522 | A1 | 10/2008 | Pappone et al. | |
| 2008/0255540 | A1 | 10/2008 | Selkee | |
| 2008/0275428 | A1 | 11/2008 | Tegg et al. | |
| 2008/0275442 | A1 | 11/2008 | Paul et al. | |
| 2008/0275465 | A1 | 11/2008 | Paul et al. | |

(56) References Cited

U.S. PATENT DOCUMENTS

| | | |
|---|---|---|
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0254083 A1 | 10/2009 | Wallace et al. |
| 2009/0287118 A1 | 11/2009 | Malek |
| 2009/0306650 A1 | 12/2009 | Govari et al. |
| 2010/0063478 A1 | 3/2010 | Selkee |
| 2010/0137845 A1 | 6/2010 | Ramstein et al. |
| 2010/0145423 A1* | 6/2010 | Seifert .................. 607/116 |
| 2010/0152574 A1 | 6/2010 | Erdman et al. |
| 2010/0168548 A1 | 7/2010 | Govari |
| 2010/0168620 A1 | 7/2010 | Klimovitch et al. |
| 2010/0168918 A1 | 7/2010 | Zhao et al. |
| 2010/0222859 A1 | 9/2010 | Govari |
| 2011/0054287 A1 | 3/2011 | Schultz |
| 2011/0054446 A1 | 3/2011 | Schultz |
| 2011/0130648 A1 | 6/2011 | Beeckler et al. |
| 2011/0160719 A1 | 6/2011 | Govari et al. |
| 2011/0184406 A1 | 7/2011 | Selkee |
| 2012/0053403 A1* | 3/2012 | Ducharme et al. ......... 600/104 |
| 2012/0143088 A1 | 6/2012 | Schultz |
| 2012/0172703 A1 | 7/2012 | Esguerra et al. |
| 2013/0006238 A1 | 1/2013 | Ditter et al. |

FOREIGN PATENT DOCUMENTS

| | | |
|---|---|---|
| EP | 928601 A | 7/1999 |
| EP | 1042990 A | 10/2000 |
| EP | 1181896 A1 | 2/2002 |
| EP | 1502555 A | 2/2005 |
| EP | 1586281 A | 10/2005 |
| EP | 1690564 A | 8/2006 |
| EP | 1743575 A | 1/2007 |
| EP | 1820464 A | 8/2007 |
| EP | 1897581 A | 3/2008 |
| EP | 2000789 A | 12/2008 |
| EP | 2047797 A | 4/2009 |
| EP | 2127604 A | 12/2009 |
| EP | 2130508 A | 12/2009 |
| EP | 2172240 B1 | 4/2010 |
| EP | 2229904 A | 9/2010 |
| EP | 2289403 A | 3/2011 |
| EP | 2289408 A | 3/2011 |
| EP | 2338411 A | 6/2011 |
| EP | 2338412 A | 6/2011 |
| JP | 2005345215 A | 12/2005 |
| JP | 2006064465 A | 3/2006 |
| WO | WO 95/10326 A | 4/1995 |
| WO | WO 96/05768 A | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 99/56812 A | 11/1999 |
| WO | WO 03/020139 A | 3/2003 |
| WO | WO 2006/003216 A | 1/2006 |
| WO | WO 2006/029563 A | 3/2006 |
| WO | WO 2006/086152 A | 8/2006 |
| WO | WO 2006/092563 A | 9/2006 |
| WO | WO 2006/092563 A1 | 9/2006 |
| WO | WO 2007/025230 A | 3/2007 |
| WO | WO 2007/050960 A | 5/2007 |
| WO | WO 2007/067938 A | 6/2007 |
| WO | WO 2007/082216 A | 7/2007 |
| WO | WO 2007/098494 A | 8/2007 |
| WO | WO 2007/111182 A | 10/2007 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |

OTHER PUBLICATIONS

EP 10252116.8—2305 Search Report dated Apr. 29, 2011.

U.S. Appl. No. 12/173,150, filed Jul. 15, 2008—pending.

Biter, W.J. et al., "Magnetic Wire Strain Sensor", 33rd International SAMPE Technical Conference, Nov. 2001, vol. 33, pp. 12-23, Seattle, WA.

Biter, W.J. et al., "Magnetic Wire for Onitoring Strain in Composites", *Sensors*, Jun. 2001, www.sensormag.com, pp. 110-114.

Okumura, Y. et al., "A Systematic Analysis of In Vivo Contact Forces on Virtual Catheter Tip-Tissue Surface Contact During Cardiac Mapping and Intervention", *J. of Cardiovasc Electrophysiol*, vol. 19, pp. 632-640, Jun. 2008.

\* cited by examiner

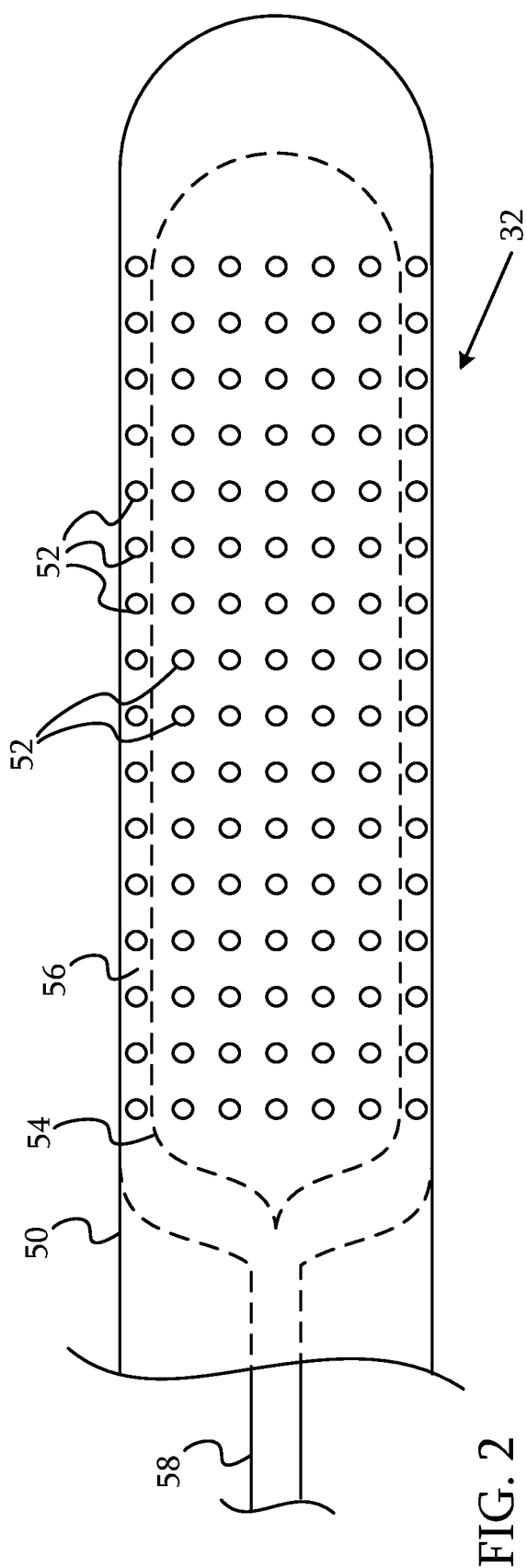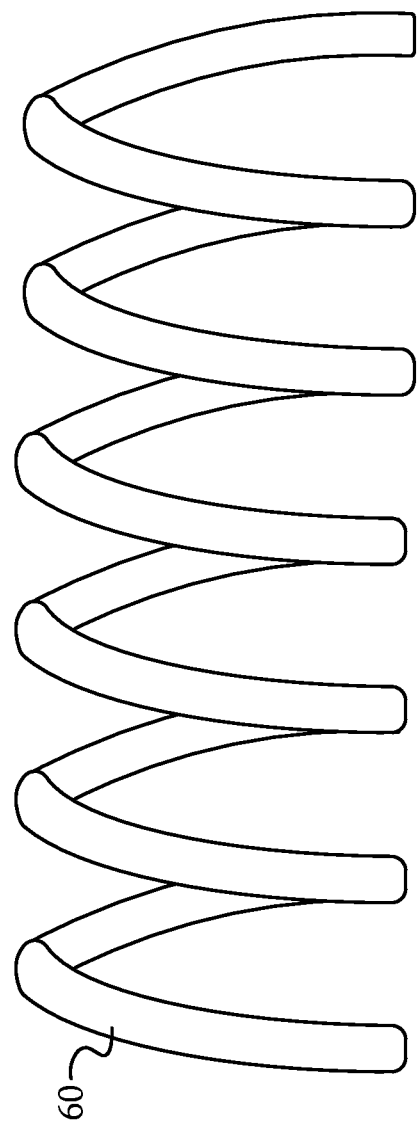
FIG. 2
FIG. 3

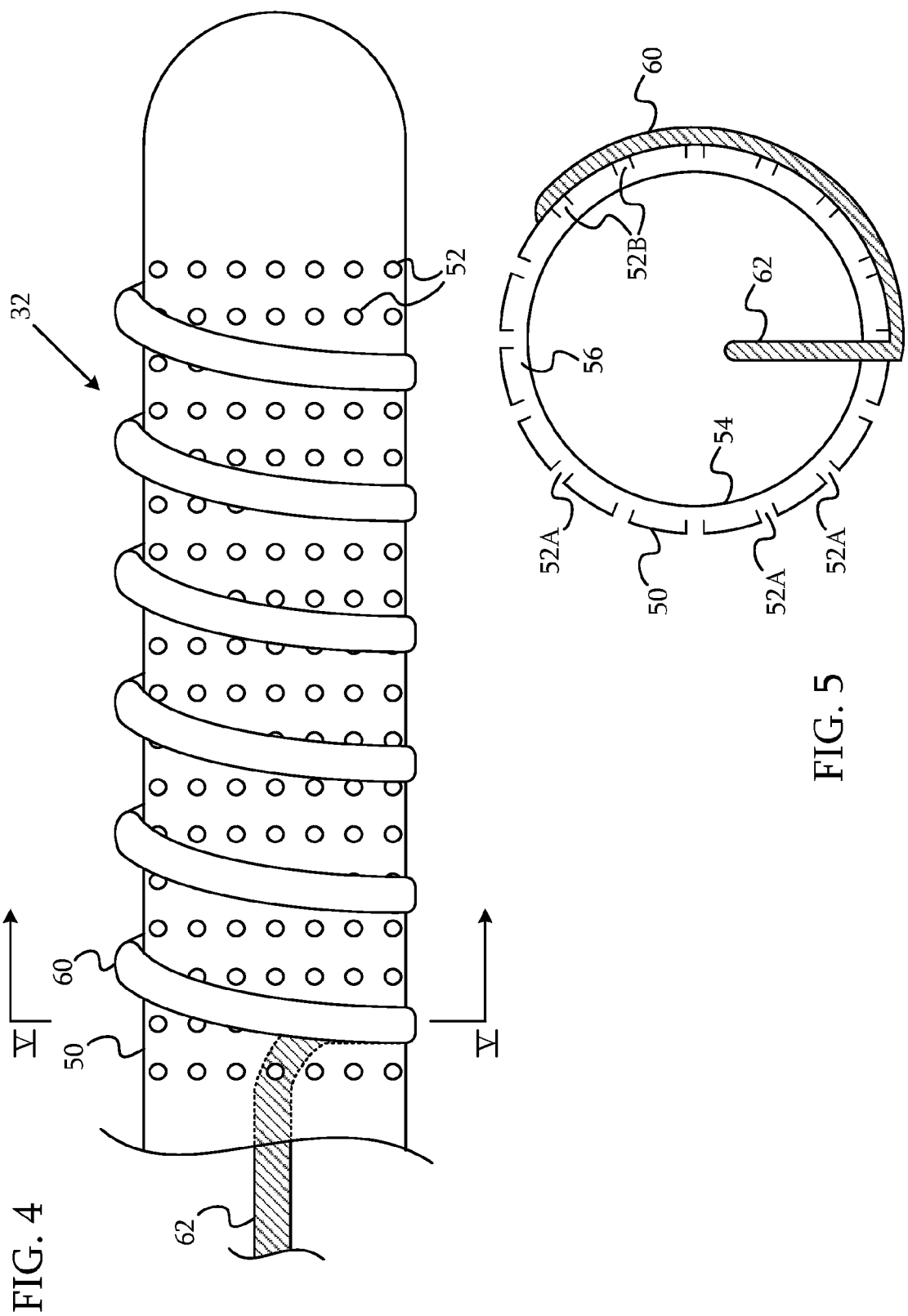

CATHETER WITH HELICAL ELECTRODE

FIELD OF THE INVENTION

The present invention relates generally to medical devices, and specifically to cooling of tissue contacted by an invasive probe within the body.

BACKGROUND OF THE INVENTION

In some medical procedures, energy is imparted to body tissue locally, in a concentrated dose, and it is desirable to cool the treatment area in order to reduce collateral tissue damage.

For example, cardiac ablation therapy is used to treat arrhythmias by heating tissue with radio-frequency (RF) electrical energy to create non-conducting lesions in the myocardium. It has been found that cooling the area of the ablation site reduces tissue charring and thrombus formation. For this purpose, Biosense Webster Inc. (Diamond Bar, Calif.) offers the ThermoCool® irrigated-tip catheter as part of its integrated ablation system. The metal catheter tip, which is energized with RF current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

SUMMARY

Embodiments of the present invention that are described hereinbelow provide irrigated probes for invasive medical procedures, such as irrigated catheters for use in RF ablation, as well as efficient methods for manufacturing such probes.

There is therefore provided, in accordance with an embodiment of the present invention, an invasive probe, including an insertion tube containing a lumen for providing an irrigation fluid and including a distal portion having a plurality of perforations therethrough providing fluid communication between the lumen and an outer surface of the insertion tube. At least one helical electrode is fitted over the distal portion of the insertion tube.

Typically, the probe includes one or more wires that pass through the tube and are electrically coupled to the at least one helical electrode. Additionally or alternatively, the at least one helical electrode covers some of the perforations.

In one embodiment, the at least one helical electrode includes multiple helical electrodes, which are distributed along the distal portion.

In a disclosed embodiment, the insertion tube is configured for insertion through a blood vessel into a chamber of a heart of a subject, so as to bring the at least one helical electrode into contact with endocardial tissue in the heart.

Typically, the plurality of the perforations includes at least eight perforations, and possibly at least fifty perforations. The perforations typically have a diameter less than 0.5 mm, and possibly less than 0.2 mm. The perforations may have respective sizes that vary depending on respective longitudinal locations of the perforations.

In one embodiment, the at least one helical electrode includes a wire coil helically wound about the distal portion of the insertion tube. In another embodiment, the at least one helical electrode includes a tube cut out along a spiral pattern.

There is also provided, in accordance with an embodiment of the present invention, medical apparatus, including a probe, for insertion into a body of a subject. The probe includes an insertion tube containing a lumen and including a distal portion having a plurality of perforations therethrough providing fluid communication between the lumen and an outer surface of the insertion tube, with at least one helical electrode fitted over the distal portion of the insertion tube and configured to contact tissue in the body. An energy generator is coupled to the probe so as to supply electrical energy to the at least one helical electrode. An irrigation pump is coupled to the lumen so as to supply an irrigation fluid via the lumen and the perforations to the tissue.

In a disclosed embodiment, the energy generator is coupled to supply electrical energy to the at least one helical electrode in order to ablate the tissue. For example, the probe may be configured for insertion through a blood vessel into a heart of the subject for ablation of myocardial tissue in the heart.

There is additionally provided, in accordance with an embodiment of the present invention, a method for treatment, including inserting a probe into a body of a subject. The probe includes an insertion tube containing a lumen and including a distal portion having a plurality of perforations therethrough providing fluid communication between the lumen and an outer surface of the insertion tube, with at least one helical electrode fitted over the distal portion of the insertion tube. The at least one helical electrode is brought into contact with tissue in the body. Electrical energy is applied through the at least one helical electrode to the tissue, and an irrigation fluid is supplied via the lumen and the perforations to the tissue.

Typically, the fluid is supplied in order to cool the distal portion and the tissue.

There is further provided, in accordance with an embodiment of the present invention, a method for producing a medical device, including creating a plurality of perforations through an outer surface of a distal portion of an insertion tube containing a lumen so as to provide fluid communication between the lumen and an outer surface of the insertion tube. At least one helical electrode, including a conductive material, is slid over the distal portion of the insertion tube. The at least one helical electrode is then affixed to the outer surface of the distal portion of the insertion tube.

The present invention will be more fully understood from the following detailed description of the embodiments thereof, taken together with the drawings in which:

BRIEF DESCRIPTION OF THE DRAWINGS

FIG. 2 is a schematic side view of a perforated catheter insertion tube, in accordance with an embodiment of the present invention;

FIG. 3 is a schematic side view of a coil electrode, in accordance with an embodiment of the present invention;

FIG. 4 is a schematic side view of the distal portion of a perforated catheter onto which a coil electrode has been fitted, in accordance with an embodiment of the present invention;

FIG. 5 is a schematic, cross-sectional view of the catheter of FIG. 4, taken along a line V-V.

DETAILED DESCRIPTION OF EMBODIMENTS

In RF electrical ablation procedures, as noted earlier, irrigating the area of the ablation site reduces tissue charring, thrombus formation, and adhesion between the ablation electrode and the tissue. Methods and devices for irrigation to date have required that the electrode itself be perforated so that irrigation fluid can pass out of the catheter through the perforations into the treatment area. A perforated electrode of this type and methods for producing the perforations are described, for example, in U.S. patent application Ser. No. 12/173,150, filed Jul. 15, 2008, which is assigned to the assignee of the present patent application and whose disclosure is incorporated herein by reference. Creating the perforations is time-consuming and costly, however, and may weaken the electrode structure.

Embodiments of the present invention that are described hereinbelow provide a simple, inexpensive method for producing ring electrodes with irrigation. An invasive probe, such as a catheter, is produced with multiple perforations through its outer wall in the area in which a ring electrode is to be placed. The perforations communicate with a lumen inside the probe, which conveys irrigation fluid to the perforations. A conductive coil electrode, typically having the form and resilience of a helical spring, is fitted over and fixed to the probe at the desired electrode location. This coil electrode is connected to one or more wires running through the probe, which may be used, for example, to provide RF electrical energy to the coil for ablation therapy. Although the placement of the coil electrode will typically cover some of the perforations in the wall of the probe, other perforations, in the gaps between the turns of the coil, remain uncovered. During operation, these open perforations provide irrigation throughout the treatment area.

The design described above and shown in the figures that follow is easy and inexpensive to manufacture. It provides the benefits achieved by a perforated, irrigated electrode, while avoiding the difficulty and costs of actually creating the perforations in the electrode. This sort of electrode structure can be used in creating multiple ring electrodes along the length of a catheter or other structure, such as lasso.

Figure 1:
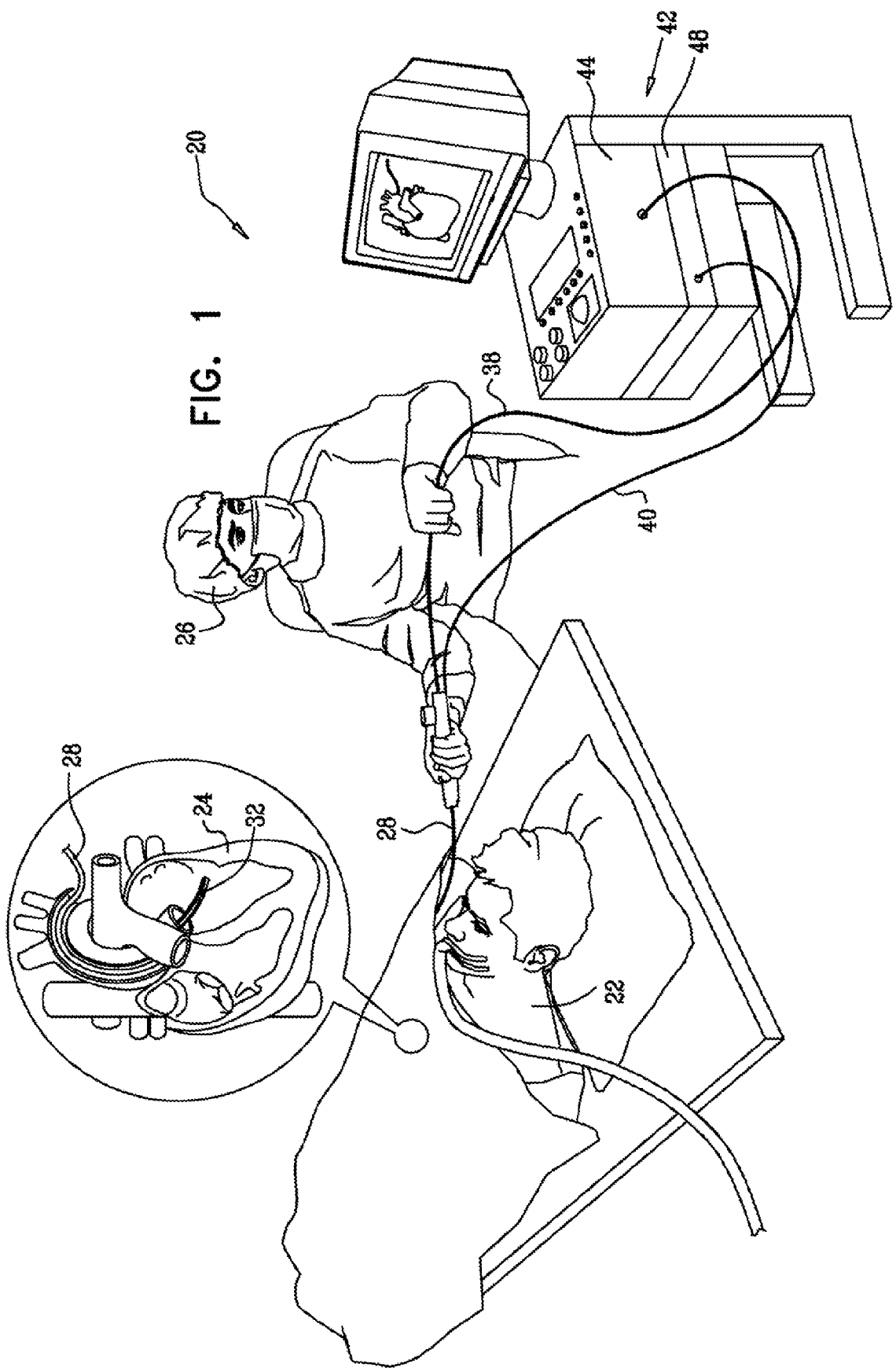
FIG. 1 is a schematic, pictorial illustration of a system for cardiac ablation therapy, in accordance with an embodiment of the present invention.

FIG. 1 is a schematic, pictorial illustration of a system 20 for cardiac ablation therapy, in accordance with an embodiment of the present invention. An operator 26 inserts a catheter 28 through a blood vessel into a chamber of a heart 24 of a subject 22, and manipulates the catheter so that a distal portion 32 of the catheter contacts the endocardium in an area that is to be treated. The distal portion of the catheter is perforated to enable irrigation of the treatment area, as shown and described hereinbelow. In other respects, however, system 20 resembles systems for cardiac ablation treatment that are known in the art, such as the above-mentioned Biosense Webster system, and the components of such systems may be adapted for use in system 20.

After positioning distal portion 32 of catheter 28 at an ablation site, and ensuring that an electrode on the distal portion (as shown below) is in contact with the endocardium at the site, operator 26 actuates a radio frequency (RF) energy generator 44 in a control console 42 to supply RF energy via a cable 38 to the electrode. Meanwhile, an irrigation pump 48 supplies a cooling fluid, such as saline solution, via a tube 40 and a lumen in catheter 28 to the distal portion. Operation of the RF energy generator and the irrigation pump may be coordinated in order to give the appropriate volume of irrigation during ablation, so as to cool the electrode and the tissue without overloading the heart with irrigation fluid. A temperature sensor (not shown in the figures) in distal portion 32 may provide feedback to console 42 for use in controlling the RF energy dosage and/or irrigation volume.

FIG. 2 is a schematic side view of a portion of an insertion tube 50 of catheter 28, in accordance with an embodiment of the present invention. The figure shows the distal portion of the insertion tube at a stage of manufacturing before assembly of an electrode onto distal portion 32. Tube 50 typically comprises a suitable biocompatible plastic, such as polyurethane, which is typically about 2.3 mm in diameter, with a wall thickness of about 0.15 mm. These dimensions, however, are given solely by way of illustration, and larger or smaller dimensions may be used depending on application requirements.

The outer surface of the distal portion of tube 50 is penetrated by multiple perforations 52, which are distributed over the surface of the distal tip both longitudinally (i.e., along the direction parallel to the longitudinal axis of catheter 28) and circumferentially (along circumferences around the axis). The perforations may be formed in tube 50 by any suitable method known in the art, such as pre-molding of the perforations at the time of fabrication of the tube, or punching or drilling (by laser or mechanical means) the perforations into the tube after extrusion.

Distal portion 32 contains an interior reservoir 56, which is fed with irrigation fluid by a lumen 58 inside tube 50. Perforations 52 extend between reservoir 56 and the outer surface of tube 50. In the embodiment shown in the figures, reservoir 56 has an inner surface 54, which may be formed, for example, by a fitting a tube of smaller diameter inside tube 50. Alternatively, the reservoir may occupy the entire interior space at the distal tip of tube 50, which may then be closed off by a plug (not shown) proximal to the distal tip, through which lumen 58 feeds. Alternative reservoir configurations will be apparent to those skilled in the art and are considered to be within the scope of the present invention.

Typically, tube 50 has at least eight perforations, which are less than 0.5 mm in diameter, in order to distribute the irrigation over the area of distal portion 32 both longitudinally and circumferentially without overloading the heart with the cooling fluid. The inventors have found it advantageous, however, to have at least fifty perforations in the distal portion, with diameters no greater than 0.2 mm, and possibly as small as about 0.1 mm. The sizes of the perforations may optionally be varied over the length of the distal tip to compensate for pressure variation and ensure equal flow over the entire length. For this purpose, the perforations at and near the most distal part of the tip may be made larger than the more proximal perforations, which are nearer to the fluid inlet.

FIG. 3 is a schematic side view of a coil electrode 60, in accordance with an embodiment of the present invention. This electrode is fitted over tube 50, as shown in the figures that follow. Electrode 60 typically comprises a resilient, biocompatible conductive material, such as gold, platinum or iridium wire, or an alloy of such metals. The coil electrode may comprise a wire, which is wound into a helical coil, as shown in the figure, resembling a coil spring. Alternatively, the coil electrode may be made from a tube, which is cut out along a spiral pattern to create a helical shape, using laser cutting, for example. The coil electrode has an inner diameter equal to or slightly smaller than the outer diameter of tube 50, so that the coil will fit snugly over the tube.

Reference is now made to FIGS. 4 and 5, which schematically show distal portion 32 of catheter 28, made by fitting coil electrode 60 over tube 50, in accordance with an embodiment of the present invention. FIG. 4 is a side view, while FIG. 5 is a cross-sectional view taken along the line marked V-V in FIG. 4. Electrode 60 is slid to the desired location on tube 50, and is then glued or otherwise fastened in place. One or more wires 62 inside tube 50 penetrate through the outer surface of the tube (possibly through one of perforations 52) and are soldered or otherwise bonded to electrode 60. Any suitable technique that is known in the art for electrical coupling to ring electrodes may similarly be used for this purpose. Wires 62 run through to the proximal end of catheter 28, where they connect via cable 38 to RF energy generator 44 (FIG. 1).

As can be seen in FIGS. 4 and 5, when electrode 60 is fastened over tube 50, it covers some of the perforations (marked 52B in FIG. 5). A sufficient number of the perforations (marked 52A) remain open, however, to provide adequate irrigation of the area contacted by the electrode. This arrangement is advantageous in that it obviates the need for high positional precision in forming perforations 52 in tube 50 and in placing electrode 60 on the tube. During the ablation procedure, lumen 58 (FIG. 2) conveys fluid from irrigation pump 48 (FIG. 1) to reservoir 56. The fluid exits tube 50 through perforations 52A to the surrounding tissue while electrode 60 delivers the RF energy in order to ablate the tissue.

Figure 6:
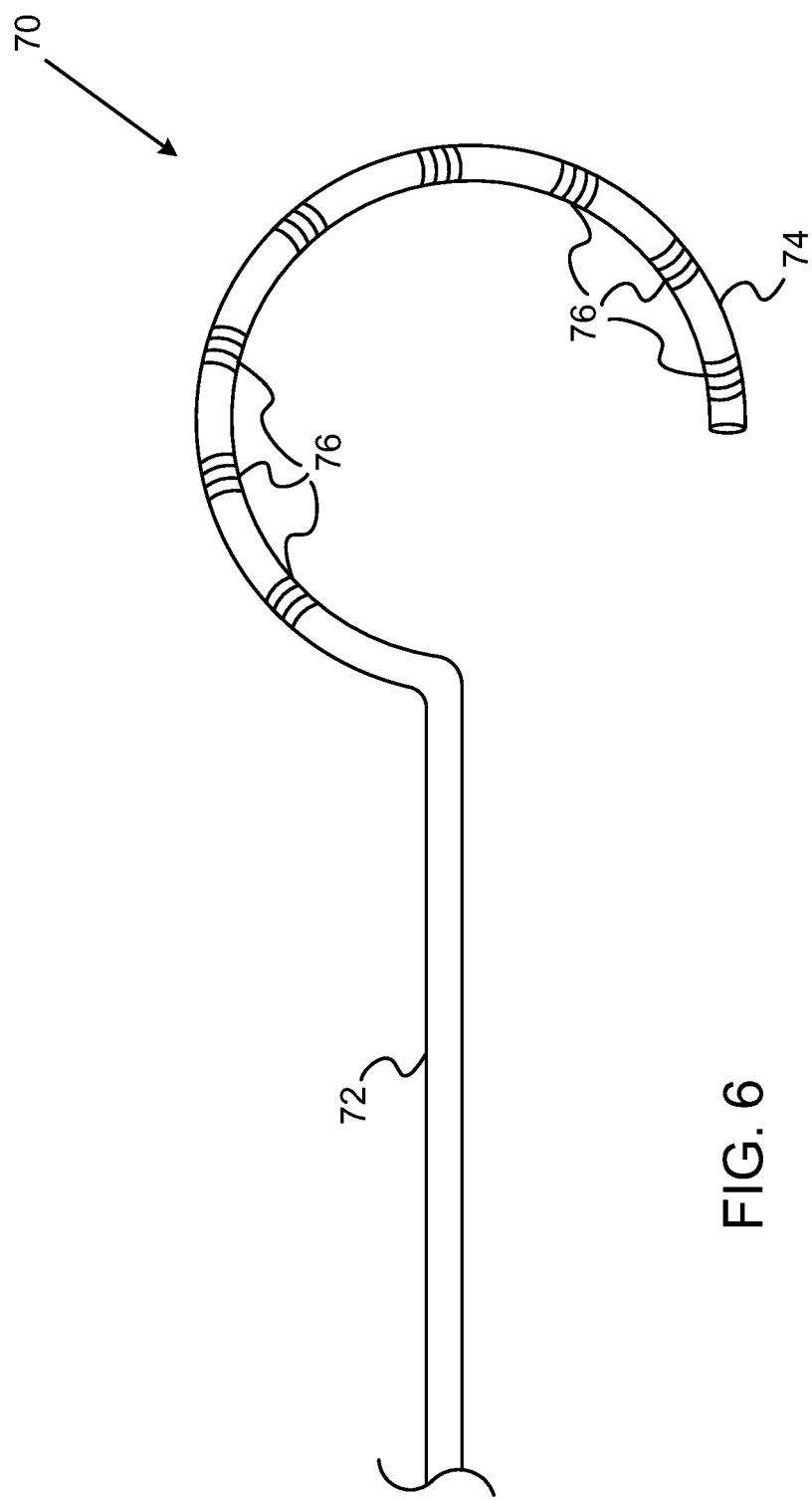
FIG. 6 is a schematic side view of a lasso catheter with coil electrodes, in accordance with an embodiment of the present invention.

FIG. 6 is a schematic side view of a lasso catheter 70 with coil electrodes 76, in accordance with an embodiment of the present invention. The lasso catheter insertion tube is formed to define a shaft 72 with a distal portion 74 having a roughly circular lasso shape. This sort of lasso shape can be used, for example, in ablating myocardial tissue along a circular path around the ostia of the pulmonary veins in treatment of atrial fibrillation.

In order to ablate multiple locations simultaneously along the desired path, electrodes 76 are distributed around the circumference of distal portion 74. Each electrode is slid into place, fastened, and connected electrically to wires inside catheter 70 in the manner described above. Distal portion 74 may also have perforations (not shown in this figure) for the purpose of irrigation, as in catheter 28. Multiple coil electrodes may likewise be distributed along the length of catheters of other types, as well as on other sorts of tubular probes.

Although the embodiments described above relate specifically to catheters used in RF ablation treatment within the heart, the principles of the present invention may similarly be applied to other organs and in other types of diagnostic and therapeutic procedures, particularly procedures that involve application of energy to body tissues. For example, a device with a similar sort of irrigated tip may be used in therapies that involve microwave-based or ultrasonic tissue heating. As another example, coil electrodes of the type described above may also be used without irrigation on catheters and tubular probes of other types.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. An invasive probe, comprising:
    an insertion tube having an outer tube surface and an inner tube surface and containing a lumen for providing an irrigation fluid, the insertion tube having a distal portion comprising an interior reservoir in fluid communication with the lumen, the interior reservoir having an interior reservoir surface and being formed between the inner tube surface and the interior reservoir surface, the distal portion having a plurality of longitudinally and circumferentially distributed perforations that extend between the reservoir and the outer tube surface of the tube providing fluid communication between the interior reservoir and the outer tube surface of the insertion tube; and
    at least one helical electrode fitted over the distal portion of the insertion tube wherein the helical electrode covers only some of the plurality of perforations thereby leaving a sufficient number of perforations open to provide irrigation fluid around the helical electrode.

2. The probe according to claim 1, and comprising one or more wires that pass through the tube and are electrically coupled to the at least one helical electrode.

3. The probe according to claim 1, wherein the at least one helical electrode comprises multiple helical electrodes, which are distributed along the distal portion.

4. The probe according to claim 1, wherein the insertion tube is configured for insertion through a blood vessel into a chamber of a heart of a subject, so as to bring the at least one helical electrode into contact with endocardial tissue in the heart.

5. The probe according to claim 1, wherein the plurality of the perforations comprises at least eight perforations.

6. The probe according to claim 5, wherein the plurality of the perforations comprises at least fifty perforations.

7. The probe according to claim 6, wherein the perforations have a diameter less than 0.2 mm.

8. The probe according to claim 1, wherein the perforations have a diameter less than 0.5 mm.

9. The probe according to claim 1, wherein the perforations have differing sizes that vary depending on the longitudinal locations of the perforations along the length of the insertion tube.

10. The probe according to claim 9 wherein the size of the perforations at the distal most end of the insertion tube are larger in diameter than the perforations that are more proximally located along the length of the insertion tube.

11. The probe according to claim 1, wherein the at least one helical electrode comprises a wire coil helically wound about the distal portion of the insertion tube.

12. The probe according to claim 1, wherein the at least one helical electrode comprises a tube cut out along a spiral pattern.

13. Medical apparatus, comprising:
    a probe, for insertion into a body of a subject, the probe comprising:
    an insertion tube having an outer tube surface and an inner tube surface and containing a lumen, the insertion tube comprising a distal portion having an interior reservoir in fluid communication with the lumen, the interior reservoir having an interior reservoir surface and being formed between the inner tube surface and the interior reservoir surface, the distal portion having a plurality of longitudinally and circumferentially distributed perforations that extend between the reservoir and the outer surface of the tube, providing fluid communication between the reservoir and the outer tube surface of the insertion tube; and
    at least one helical electrode fitted over the distal portion of the insertion tube and configured to contact tissue in the body wherein the helical electrode covers only some of the plurality of perforations thereby leaving a sufficient number of perforations open to provide adequate irrigation fluid around the helical electrode;
    an energy generator, for coupling to the probe so as to supply electrical energy to the at least one helical electrode; and
    an irrigation pump, for coupling to the lumen so as to supply an irrigation fluid via the lumen and the perforations to the tissue.

14. The apparatus according to claim 13, wherein the energy generator is coupled to supply electrical energy to the at least one helical electrode in order to ablate the tissue.

15. The apparatus according to claim 13, wherein the probe is configured for insertion through a blood vessel into a heart of the subject for ablation of myocardial tissue in the heart.

* * * * *